United States Patent [19]

Strawn

[11] Patent Number: Plant 6,469

[45] Date of Patent: Dec. 20, 1988

[54] MINIATURE ROSE PLANT NAMED WOW

[76] Inventor: Leslie E. Strawn, 10422 Morningside Ave., Garden Grove, Calif. 92648

[21] Appl. No.: 876,206

[22] Filed: Jun. 19, 1986

[51] Int. Cl.[4] ..... A01H 5/00

[52] U.S. Cl. ..... Plt./7

[58] Field of Search ..... Plt. 7

*Primary Examiner*—Robert E. Bagwill

[57] ABSTRACT

The subject of the present disclosure is a new and distinct variety of miniature rose plant characterized by deep orange buds and flowers of distinctive form and further identified by the rounded, erect, drawf, compact plant.

1 Drawing Sheet

The present invention relates to a new and distinct variety of hardy, dwarf, bush type rose plant of the miniature class, the variety being primarily characterized — as to novelty — by the deep orange buds and flowers which in general coloring effect are similar to its seed parent Anne Cocker (Floribunda — nonpatented)

The variety is further characterized by:

An abundance of bloom, with flowers borne one to a stem. No side buds. Slightly fragrant.

A plant which is vigorous, of rounded bushy growth habit, very glossy foliage with pointed leaflets; the buds and flowers being similar in form and size to Tiger Butter (Miniature — U.S. Plant Pat. No. 5,329).

The plant, which has a normal height of 12 to 14 inches, can easily be maintained at lesser height by occasional trimming.

A plant which grows and blooms satisfactorily both in a greenhouse or outdoors; is good for growing in pots; and provides excellent garden decoration as well as cut flowers.

The present variety of miniature rose was originated by me in my home greenhouse, located at Garden Grove, Orange County, Calif., under conditions of careful control and observation, as a cross between Anne Cocker (Floribunda — nonpatented) as the seed parent and an unnamed seedling as the pollen parent. The unnamed seedling was derived from a cross of Puerto Rico (Floribunda—U.S. Plant Pat. No. 3,519) as the seed parent and Darling Flame (Miniature — nonpatented) as the pollen parent.

Subsequent to origination of the variety I successfully asexually reproduced it in my garden, located as foresaid, (Also propagated by Pixie Treasures Rose Nursery, 4121 Prospect Ave., Yorba Linda, Orange County, Calif.) by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate indentifications being by reference to the British Colour Council Horticultural Colour Chart, except where common terms of color definition are employed.

Type: Hardy; dwarf; bushy; rounded; upright; seedling; greenhouse; outdoors; cut flowers; garden decoration; pot plant.

Class: Miniature.

*Variety name.*—Wow!.

*Generic name.*—Pixiwow.

Flowers borne: Singly on upright, slender stems.

Quantity of Bloom: Abundant, both outdoors and in the greenhouse.

Bud:

*Peduncle.—Medium length,* 2–2½ cm; erect, straight, slender, sturdy; bronze in color; few or many glands; no hairs.

*Size.*—Before calyx breaks — 1¾ to 2 cm length.

*Form.*—Pointed; foliaceous parts extend beyond tip of bud one third or more than its length.

*Color.*—Green and bronze. As calyx breaks — color of outside petal showing close to—Saturn red 13/1.

Bloom:

*Size.*—When fully open — small, averaging 4½ to 5 cm.

*Petalage.*—Double, averaging 25 to 30 petals, arranged symmetrically, with a few petaloids close to stamens.

*Form.*—Ovoid. As petals open symmetrically they remain in their upright position, with topmost edges of petals flairing outward. When fully open outside petals reflex back at side edges.

Petals:

*Substance.*—Moderately thick and of good substance.

*Texture.*—Smooth and satiny on both surfaces. Slightly viened. *Shape.*—Outside petals: Broad with small point at apex. Pointed base. Intermediate petals: Same as outside petals. Inside petals: Same as intermediate petals but narrower. Petaloids: Two to three close to stamens.

Color: One half to three-quarters open flowers from plants grown outdoors at Pixie Treasures Rose Nursery, Yorba Linda, Calif., April 1986.

*Outside petal.*—Outside surface: Close to Saturn red 13/2 blending deeper in the outer third to near Saturn red 13/1. Base yellow light. Inside surface: Close to Indian orange 7 13/1. Base light yellow.

*Intermediate petal.*—Outside surface: Same as outside petal. Same base Inside surface: Same as outside petal. Same base.

*Inside petal.*—Same as outside and intermediate petals. Same base.

General color effect:

*Newly open flowers.*—Symmetrically arrangement of petals of Indian orange with the lighter tones of Saturn red of the outside surfaces giving a moderate two-tone effect; the yellow base being evident at different stages of bloom.

*Three to four days open.*—Keeps its symmetry fully open with stamens showing. Color changes to a shade close to Vermilion 18/1 or 18/2 from exposure to sunlight.

Behavior: Opens well in all weather. Petals tend to hang on for 5 to 6 days then fall; calyx remains and forms (usually) a hip. *Flower longivity* (April 1986).—Plant in pot — 3 to 4 days; plant in ground — 4 to 5 days; cut flowers at living room temperature — 3 to 4 days.

Reproductive organs:

*Stamens.*—65 to 70.

*Filaments.*—Uneven lengths; light yellow.

*Anthers.*—Golden; introse and antrose.

*Pollen.*—Moderate amount.

*Pistils.*—Projects above disc.

*Styles.*—Several, bunched; 2 mm length, reddish.

*Ovaries.*—Enclosed in calyx.

*Hips.*—Usually form from self pollenization.

*Sepals.*—Spear shaped, reflexed; three fringed, two plain.

*Seeds.*—Usually three to five.

Foliage:

Leaves.—Compound of five leaflets; length 5 to 6 mm; very glossy.

*Leaflets.*—Broad lanceolate; supported by a short petiolule.

*Rachis.*—Length 3 cm; upper side grooved; under side 2 or 3 minute thorns.

*Stipules.*—Short with slender pointed auricles, flairing outward at approx. 60 degrees.

*Color.*—Dark green; rachis and veining dark red on new foliage.

Growth:

*Habit.*—Dwarf, upright and rounded; 30 to 35 cm (12 to 14 in.).

*Growth.*—Vigorous; length between internodes — 2 cm or less; much branched.

*Canes.*—Slender and sturdy.

*Main stems.*—Medium green.

*Branches.*—Medium green; new growth reddish green; much branched.

*Thorns.*—3 to 5 mm length; needle declining; dilated at base; varying sizes; some branches may be thornless.

*New shoots.*—Dark reddish green.

The following is claimed:

1. A new and distinct variety of miniature rose plant, hardy, dwarf, bushy, upright, rounded, much branched habit, substantially as illustrated and described, characterized by buds and flowers which are in a color hue similar to Anne Cocker (Floribunda — non-patented) and giving the coloring effect of bright orange and resembling Tiger Butter (Miniature — U.S. Plant Pat. No. 5,329) in form and size, having buds and flowers of a distinct and unusual appearance as compared to other miniature rose plants; said flowers being fully double, unique in an ovoid from and further characterized by its vigor, abundance of bloom and foliage and ease of propagation from soft wood cuttings and by budding.

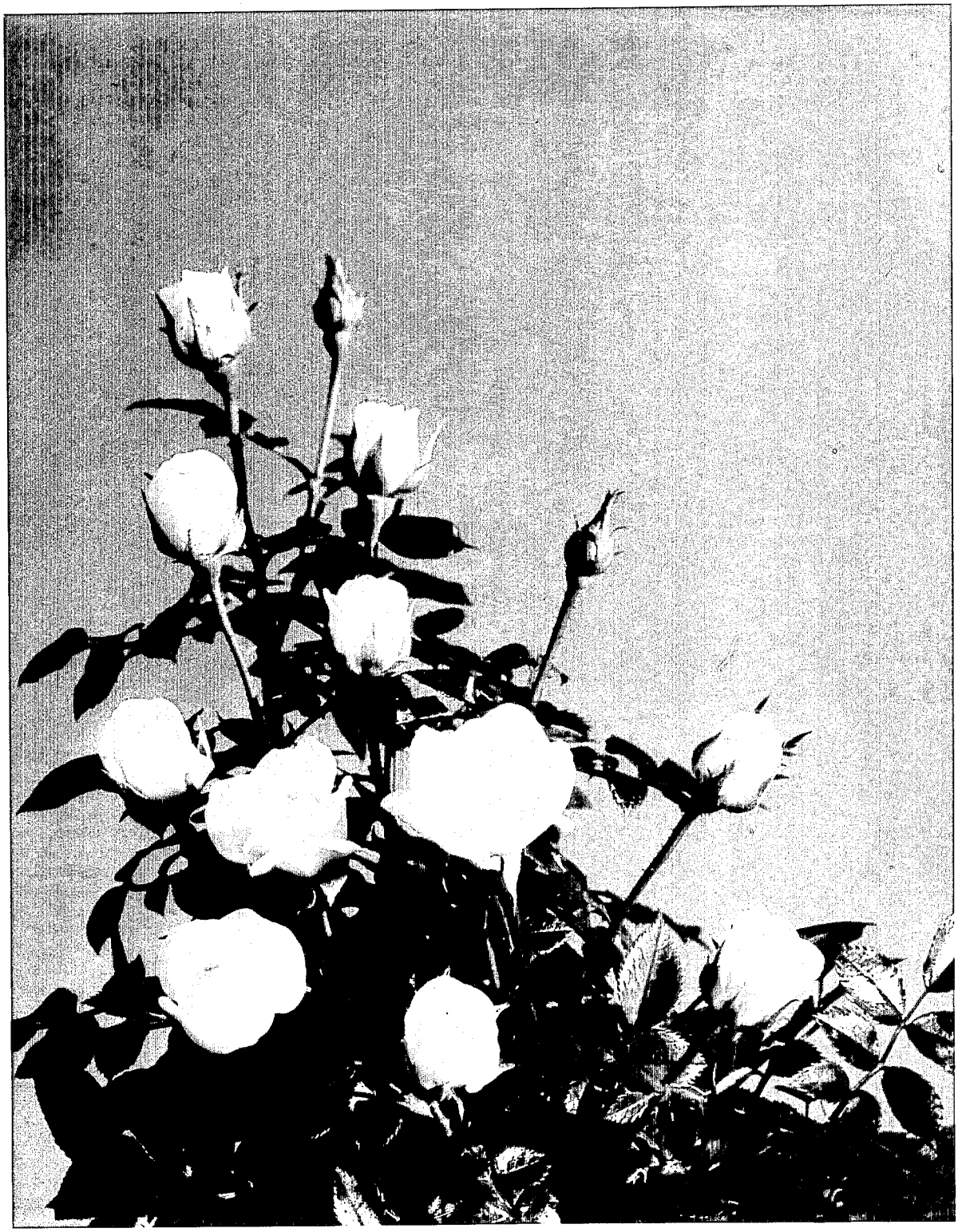

* * * * *